United States Patent [19]

Osther

[11] Patent Number: 5,008,183
[45] Date of Patent: Apr. 16, 1991

[54] ASSAY SYSTEM FOR DETECTING ANTIBODY AND A METHOD OF PRODUCING NON-HUMAN IMMUNE ANTIBODY

[75] Inventor: Kurt B. Osther, Dallas, Tex.
[73] Assignee: Bio-Research Laboratories, Inc., Dallas, Tex.
[21] Appl. No.: 192,241
[22] Filed: May 10, 1988
[51] Int. Cl.⁵ .......................................... G01N 33/569
[52] U.S. Cl. ...................... 435/5; 435/7.32; 436/513; 436/532; 436/547; 436/815; 530/387; 530/830
[58] Field of Search .............. 435/5, 7; 436/513, 532, 436/547, 815; 530/387, 830

[56] References Cited

U.S. PATENT DOCUMENTS

| | | | |
|---|---|---|---|
| 4,132,769 | 1/1979 | Osther | 436/543 |
| 4,474,877 | 10/1984 | Imagawa et al. | 436/513 X |
| 4,487,714 | 12/1984 | Kato et al. | 530/391 |
| 4,661,445 | 4/1987 | Saxinger et al. | 436/528 X |
| 4,725,669 | 2/1988 | Essex et al. | 530/395 X |
| 4,774,175 | 9/1988 | Chang et al. | 436/811 X |

OTHER PUBLICATIONS

Kalheider et al., "Porcine Immunoglobulins. I. Identification of Classes and Preparation of Specific Antisera", J. Immunol. 109(5)992-998 1972.

Thorn et al., "Enzyme Immunoassay Using Novel Recombinant . . . ", J. Clin., Microbiol. 25(7), 1207-1212 (Jul. 1987).

Primary Examiner—Christine Nucker
Attorney, Agent, or Firm—Bryan, Cave, McPheeters & McRoberts

[57] ABSTRACT

An improved assay method for detecting the presence of an antibody capable of binding with an antigen of a virus is provided. The improvement comprises using a non-human immune antibody which is reactive with an anti-human antibody as a positive control in the assay. Non-human immune IgM and a method of producing the IgM is also provided.

12 Claims, 1 Drawing Sheet

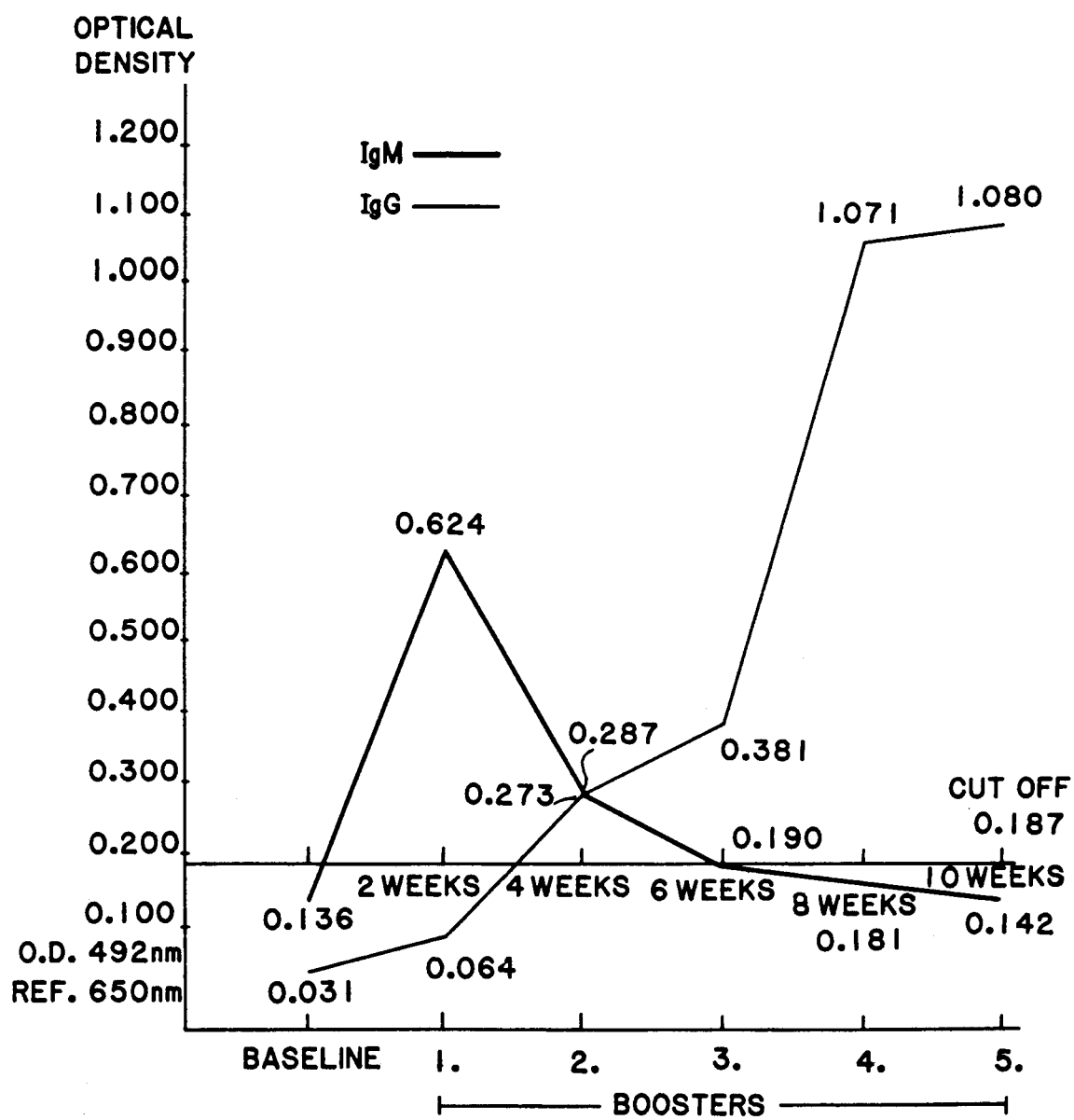

ASSAY SYSTEM FOR DETECTING ANTIBODY AND A METHOD OF PRODUCING NON-HUMAN IMMUNE ANTIBODY

TECHNICAL FIELD

The present invention relates to the use of a non-human immune antibody, which is capable of reacting with an anti-human antibody, in an assay system for detecting the presence or absence of antibodies to viral and/or bacterial infective agents. In particular, the invention pertains to the use of porcine immune IgG and porcine immune IgM, as a positive control in an assay system. The present invention also pertains to non-human immune IgM, preferably porcine immune IgM and a method of producing it.

BACKGROUND OF THE INVENTION

Assay systems capable of detecting the presence or absence of antibodies generated in response to the presence of antigens are well known. Such assay systems have proved useful in, inter alia, the diagnosis of various diseases. For example, viral infections, such as AIDS (acquired immune deficiency syndrome) and CMV (cytomegalovirus) may be diagnosed with assays which detect the presence of viral antibodies in patients suspected of having the disease. Examples of such assay systems which employ antigen-antibody binding include ELISA, Western Blot, Quick Western Blots (U.S. Pat. Nos. 4,816,387 and 4,885,235) and RIA. Such diagnostics uniformly include controls to insure the integrity of the test system.

Typically, the diagnostics have both positive and negative controls. The positive control provides pertinent information concerning the activitY of the test system, i.e., that reactive antibodies specific to the antigens used in an antibody test system are bound to the antigens (indicating that the antigens used in the test system are working properly), and that the anti-immunoglobulin used to detect the bound immunoglobulin is working. In the case of an ELISA system the anti-immunoglobulin may be labeled with an enzyme (conjugate) which activates a substrate added to the system to give a chromogen reaction; in this case the positive control indicates whether the conjugate has reacted, and whether the substrate has worked properly as an activated chromogen. A negative control provides information about the absence of reactive antibodies specific to the particular antigens used in a test system. It also provides information as to the reaction level, determined by the signal used in a particular test, at which a specimen may be considered negative.

The cut-off point in a particular test is often based upon the relative value obtained by a positive control and/or by the negative control. An acceptable detection range obtained by the controls utilized with a particular type of test kit is specifically designed and titrated for that tYpe of kit. The positive control "value" obtained in a particular test system affects the sensitivity of that test system; the negative control "value" affects the specificity of the test system.

Presently, the antibody used for a positive control is obtained from seropositive human donors. As can be appreciated, it is disadvantageous to depend upon seropositive donors as the sole source of antibody required for a positive control. Notably, the supply of antibodies is scarce and uncertain and the quality and characteristics of the antibody varies from donor to donor. Further, as more successful therapies become known and used, fewer seropositive donors will be available, and thus the required antibody even more difficult to obtain.

In the case of AIDS patients it has been found that the condition of patients who donate blood or are subjected to plasmaphoreisis deteriorates rapidly. Therefore, obtaining AIDS positive blood or plasma from patients can accelerate the disease and accordingly, using AIDS patients as a source of antibody for use as a positive control should be avoided.

The previously mentioned assay systems detect the presence or absence of IgG (immunoglobulin G). Such assays only allow "controlled" detection (measurement defined by use of anti-IgG conjugate and of antibody positive control) of the presence of IgG in blood and body fluids directed to antigens used in the test systems. The appearance of detectable IgG directed to antigens in an infected/immunized individual does not occur until 30–40 days after initial infection in many instances. The IgG class antibodies are often present for months or years after infection/immunization.

The presence of circulating IgG directed to immunizing antigens during the course of an infection (or after immunization) is preceded by the presence of circulating IgM antibodies directed towards the antigens/immunogens. IgM antibodies directed to antigens in an infected/immunized individual are often present in detectable quantities as early as 14 days (or earlier) after the infection/immunization. The IgM class antibodies gradually lose titer 30–35 days after initial infection/immunization.

It is widely recognized that diagnostics which can detect antibodies other than IgG are desirable. For example, it is known that generally after confrontation with a foreign body, the human immune system responds by generating antibodies against the foreign body or antigen. It is believed that IgM, not IgG is produced first. As can be appreciated, assays capable of detecting IgM will facilitate early detection of numerous diseases. IgM is, however, a relatively short-lived antibody. While it may be produced shortly after infection, IgM levels fall, eventually below detectable levels, as IgG is produced, in increasing amounts. See FIG. 1 which compares the titer of IgM and IgG in a pig immunized with HIV-1. Because IgM has a short life span, IgM levels are typically below detectable levels before many diseases are even diagnosed. Therefore, IgM is not readily obtainable from seropositive donors and a dependable, reliable source of this important antibody is needed.

The present invention overcomes the previously mentioned disadvantages because it provides the ability to produce the desired antibody, i.e., IgG and IgM in a non-human species. In accordance with the present invention there is provided a method of using non-human immune antibody as a positive control in assay systems.

SUMMARY OF THE INVENTION

The present invention provides a use for non-human immune antibody in an improved assay system for detecting the presence or absence of antibody which binds with viral antigen. In an assay for detecting the presence or absence of an antibody which binds to an antigen of a human retrovirus comprising the steps of (1) sequentially contacting the antigen with a biological fluid and positive control comprising an antibody to the antigen for times and under conditions sufficient for the antigen and any antibody in the biological fluid, and the antigen and antibody in the positive control to form antigen-antibody complexes and (2) detecting the formation of the complexes, the improvement comprises the use of a positive control comprising a non-human immune antibody, the non-human immune antibody is reactive with an anti-human antibody.

It is presently preferred to use mammalian immune IgG and/or IgM and most preferably porcine immune IgG and/or IgM as a positive control in the assay.

The present invention also provides non-human immune IgM antibody and a method for producing such IgM.

It has been found, in accordance with the invention, that in both HIV-1 and in HTLV-I lysates immunized animals IgM directed to viral antigens may be detected as early as 12–15 days after immunization. IgM is still detectable 30–40 days after immunization. At that time IgG directed to the viral antigens (30–40 days after immunization) is still measurable. It is anticipated that in humans IgG antibodies directed to HIV-1 do not appear until, at the earliest, about 4 weeks after infection.

DETAILED DESCRIPTION OF THE INVENTION

Producing Immune Antibodies

In accordance with the present invention, the non-human immune antibody is obtained by immunizing an animal with viral material against which it is desired to raise a specific antibody. Examples of suitable immunizing agents include HIV-1, HIV-2, HTLV-I, HTLV-II, CMV and Epstein-Barr Virus. Of course, other immunizing agents as may be known to those skilled in the art are also useful.

The immunization procedure begins with a first vaccination of the animal with a preparation comprising 10–500 ug of viral lysate or selected portions of the viral core or envelope proteins. The viral material is preferably solubilized in Triton X-100, SDS (sodium dodecyl sulfate), mercaptoethanol, and/or Nonidet P40 detergent, and suspended in phosphate buffered saline (PBS), pH 7.2–7.4. It is presently preferred to premix 0.1–5% Triton X-100 with the PBS to elicit an optimum immune response. The first injection contains an adjuvant; Freund's complete adjuvant is preferred for this purpose. Of course, other adjuvants known to those skilled in the art may also be used. The first vaccination typically comprises a total volume of 2 ml, one ml of viral material in buffer plus one ml of adjuvant. The viral material and adjuvant should be thoroughly mixed immediately prior to injection. In a preferred embodiment, the first vaccination contains 50–100 micrograms of viral material in 1.0 ml of PBS-Triton X-100 mixed with 1.0 ml of Freund's complete adjuvant.

Booster immunizations are generally prepared without adjuvant. These injections typically contain 10–500 ug of viral proteins, preferably from about 50–100 ug per injection in PBS, pH 7.2–7.4. The lysate can be solubilized in detergents, e.g., Triton X-100. Booster injections begin from about 7 to 30 days after the initial vaccination and every 7 to 30 days thereafter until the desired antibody titer is measured, i.e., a sufficiently high titer is indicated by an OD value at least equal to a positive control reading on an ELISA test system. For example, in the ElectroNucleonics (VIRGO) HIV-1 Antibody ELISA system an HIV-1 positive control serum has an OD value of over 0.250 and under 1.000 (at 492 nm with a 650 nm reference) measured on a Behring Processor II.

It should be understood that optimal antibody titers may vary depending upon the virus used as an antigen and the particular test system used. The IgG positive control and the IgM positive control should be capable, in a certain dilution, of producing an OD value within the OD ranges given for a positive control in the individual types of known test kits (to be determined for each type of test kit) containing viral antigens for which the positive control is to be used. For example, a nonimmunized control pig serum produces an OD value, which is under the cut-off at the same dilution at which a pig positive control serum gives an acceptable positive value (e.g., for HIV-1 A6 ELISA VIRGO ENI, between 0.25–1.100).

The antibody titer is checked periodically, typically every 14 days or just prior to administering booster injections. A first blood sample is generally drawn and tested prior to the initial vaccination to establish a baseline antibody level.

It is presently preferred to vaccinate by subcutaneous injection, but other modes of administration, such as intramuscular injection may be used. The vaccination site is preferably the side of the neck, typically injecting three to four different locations. Vaccination on the neck is considered to yield higher antibody titers, but other vaccination sites as are known to those skilled in the art are suitable for raising the desired immune antibody.

Once the desired antibody titer is measured, blood from the immunized animal is collected, either by bleeding or sacrificing the animal and collecting its blood. When raising IgM antibody, to insure sufficient high antibody titer for use as a positive control, it is preferred to sacrifice the animal and harvest its blood for separation of serum when the pig serum tested shows an OD value which is within the range of a positive control, when tested in different test systems. However, it is preferable to harvest all the pig blood when the pig serum shows maximum OD value for the particular class of immunoglobulins (IgM or IgG) when the other class of immunoglobulins is below the cut-off point.

The collected blood or serum extracted therefrom is treated before use to inactivate any live virus. It is presently preferred to photochemically treat the blood or serum with Psoralen followed by U.V. irradiation. Other methods such as gamma irradiation or heat inactivation (56° C. for one hour) may also be used. It should be understood, however, that heat inactivation may adversely affect antibody titer and may not be as effective in inactivating virus as the other methods.

It is presently preferred to use serum from the immunized animal as a positive control in an assay system. However, whole blood, plasma or any other form of antibody as may be known to those skilled in the art is also useful. Before use, it is presently preferred to filter and sterilize the blood or serum and then freeze aliquots for later use; alternatively, the serum may be freeze-dried or fractionated to enrich the IgG or IgM fractions.

The previously described method can be used to produce antibody against several viruses including HIV-1, HIV-2, HTLV-I, HTLV-II, cytomegalovirus, Epstein-Barr virus, and hepatitis B virus. It is also considered within the scope of the invention to produce antibodies against a variety of bacteria such as *E. coli*, Salmonella, Tetanus, Streptococcus, and Neisseria.

The following examples are considered illustrative of the present invention.

EXAMPLE 1

Porcine Immune IgG Against HIV-1

A 60 lb mixed Yorkshire breed pig was immunized (by subcutaneous injections in the left side of the neck) with 50 ug of solubilized HIV-1 antigen lysate, psoralen—U.V. irradiation inactivated, in 1 ml of PBS-Triton X-100 and 1 ml of Freund's complete adjuvant. Just prior to injection blood was drawn from an ear vein and tested for the presence of IgG and IgM antibodies to HIV-1.

Booster injections contained 50 ug of HIV-1 viral lysate in 1 ml of PBS buffer containing lysing detergents such as Triton X-100. The first booster was administered 14 days after the first immunization, and a second booster 14 days later. The pig received a total of 5 vaccinations before it was sacrificed and its blood was harvested, and the serum was used as IgG against HIV-1. Prior to each booster, ear vein blood samples were drawn (and designated Booster #1 and Booster #2, etc.) IgG and IgM antibody titers were measured.

The presence of IgG anti-HIV-1 was measured using the ENI HIV-1 ELISA VIRGO system, following the method described by the manufacturer. The IgM anti-HIV-1 was measured using a modification of the ENI system. The modification comprised substituting affinity purified goat anti-human IgM $\mu$ change specific, labelled with alkaline phosphatase (available from Calbiochem, Catalog #401902) for the anti-IgG conjugate normally used. P-Nitrophenyl phosphate tablets, prepared in accordance with the manufacturer's instructions, were used as the substrate (P-Nitrophenyl phosphate tablets are available from Bio-Rad, Catalog #172-1063). The incubation times and washing procedure were performed as directed in the ENI package insert. The results of the IgM class were read on the Behring ELISA Processor II at 405 nm with a 650 nm Reference (see FIG. 1). The test results are plotted on FIG. 1, which is a graph plotting the OD values of IgG and IgM specific anti-HIV-1 against time.

As may be seen in the drawing, IgM is detectable before IgG. IgM peaks at about day 14 and falls to below detectable levels by day 42.

Based on the antibody titer indicated by the OD value at Booster #3, the pig's blood contained an antibody titer sufficient for use as an IgG class positive control 42 days after vaccination. It is presently believed that between two and six booster injections are required to reach antibody titers in the optimal range.

EXAMPLE 2

Producing IgG Specific Anti-HIV-1

A 60 lb mixed Yorkshire breed pig was immunized as described in Example 1 with 50 ug of solubilized HIV-1 antigen lysate. Five booster injections, each containing 50 ug of viral lysate, were administered every fourteen days, beginning 14 days after the first injection. Blood samples were drawn from the pig's ear vein prior to the first vaccination to obtain baseline antibody levels, and prior to administering each booster injection. The pig was sacrificed at day 60 and its blood collected. Serum was separated, sterile filtered and frozen. Upon testing the serum showed a high titer of IgG specific anti-HIV-1 (O.D. about 1.800) with IgM below detectable levels.

The serum collected is thus useful as a positive control in an assay for detecting antibodies which bind with HIV-1.

The following test results were obtained:

|  | Pig IgG Anti HIV-1 | Cut-Off | Human HIV-1 Ab Positive Control (ENI) |
| --- | --- | --- | --- |
| Baseline* | 0.012–0.017 | 0.273 | 0.791 |
| Booster #1 | 0.103 | 0.250 | 0.650 |
| Booster #3 | 0.750–0.800 | 0.260 | 0.497 |

IgM antibodies specific to HIV-1 were measured at Booster #3 and were found to be below cut-off (OD=0.113). Thus, IgM was below cut-off by day 42.

For purposes of this Example, IgG was measured using an HIV-1 Ab-IgG kit from ElectroNucleonics Inc. (ENI) in accordance with the manufacturer's instructions. IgM was measured using a modification of the HIV-1 ENI test kit. The IgM was measured using the method described in Example 1

EXAMPLE 3

Porcine Immune IgM Against HTLV-I

A 60 lb mixed Yorkshire breed pig was immunized (by subcutaneous injections in the left side of the neck) with 100 ug of HTLV-I viral lysate solubilized with Triton X-100 in 1 ml of PBS and 1 ml of Freund's adjuvant. No booster injections were administered. Ear vein blood samples were drawn prior to vaccination, 12 days and 17 days after vaccination. The pig was sacrificed at day 17 and its blood collected. The serum was separated, filter sterilized and frozen. Upon testing the serum showed the presence of IgM specific anti-HTLV-I at a level sufficient for use as a positive control. IgG was below detectable levels.

For purposes of this example IgG was measured using an HTLV-I Ab test kit from DuPont. The anti-IgG conjugate in the DuPont Test Kit is alkaline phosphatase (the substrate is supplied with the test kit). IgM was measured using a modification of the HTLV-I DuPont Test Kit in which the anti-IgG conjugate was substituted by an anti-IgM alkaline phosphatase used at a 1:10 dilution (Calbiochem, Catalog #401902).

The following results were obtained:

|  | IgM* | IgG* |
| --- | --- | --- |
| Baseline |  |  |
| Day 12 | 1.283 | 0.030 |
| Day 17 | 2.200 | 0.300 |

*The cut-off had an OD value of 0.522 and the IgG positive control had an OD value of 0.979.

EXAMPLE 4

Procine Immune Against HIV-1

A 60 lb mixed Yorkshire pig was vaccinated with 50 ug of HIV-1 viral lysate as previously described in Example 1. The viral lysate was purified by sucrose gradient centrifugation at approximately 100,000× g (4° C. for one hour) on an ultracentrifuge.

Blood samples were drawn prior to the first immunization 13 days and 15 days after vaccination. No booster immunizations were required. The pig was sacrificed at day 15. The blood samples collected were tested for IgG specific anti-HIV-1 proteins using an HIV-1 Antibody ELISA available from ElectroNucleonics (ENI). The blood samples were also tested for the presence of IgM using a modified ENI test kit. The modification comprised substituting affinity purified goat anti-human IgM, μ chain specific, labelled with horseradish peroxidase (available from Calbiochem, Catalog #401905) for the anti-IgG conjugate normally used. The substrate supplied with the ENI kit was used in accordance with the manufacturer's instructions. The incubation times and washing procedure were performed as directed in the ENI package insert. The results were read on a Behring ELISA processor at 492 nm with a 650 nm reference.

The results were as follows:

|  | Optical Density* | |
|---|---|---|
|  | IgG | IgM |
| Baseline | 0.042 | 0.085 |
| Day 13 | 0.051 | 0.623 |
| Day 15 (after sacrifice) | 0.053 | 0.796 |

*The cut-off value was OD 0.192; the IgG positive control value was OD 0.921.

The results show that the collected blood had a high IgM antibody titer but was not contaminated by IgG specific anti-HIV-1, and therefore is useful as a positive control in an assay for detecting IgM specific anti-HIV-1.

In producing porcine immune IgM specific antibody, it has been found that an antibody titer within the optimum range is obtainable within 14–40 days. It is presently believed that initial vaccination, without subsequent booster injections, is sufficient to obtain the desired result. However, it should be understood that one or more boosters may be required depending on the animal immunized. The need for any such boosters can be determined by carefully monitoring levels of both IgM and IgG. Such monitoring is also necessary to insure obtaining blood containing sufficiently high levels of IgM but undetectable levels of IgG.

While preferred embodiments of the invention have been described, it will be apparent to those of ordinary skill in the art that various changes and modifications may be made therein without departing from the spirit and scope of the invention. Accordingly, the above description should be construed as illustrative, and not in a limiting sense, the scope of the invention being defined by the following claims.

I claim:

1. In an assay for detecting the presence or absence of a human antibody which binds to an antigen of a virus or a bacteria, comprising the steps of:
    (a) contacting a sample of the antigen with a test sample of human biological fluid for times and under conditions sufficient for the antigen and any antibody present in the human biological fluid to form antigen-antibody complexes;
    (b) at the same time contacting another sample of the antigen with a positive control comprising a procine antibody to the antigen under the same times and conditions as in step (a), said times and conditions being sufficient for the antigen and the non-human antibody in the positive control to form antigen-antibody complexes; and
    (c) detecting the formation of any antigen-antibody complexes in steps (a) and (b) by simultaneously contacting an anti-human antibody with any antigen-antibody complex as formed, for times and under conditions sufficient for any antigen-antibody complexes formed in step (a) and step (b) to react with the anti-human antibody.

2. The assay of claim 1, wherein the non-human immune antibody comprises IgG, IgM or mixtures thereof.

3. The assay of claim 1, wherein the non-human immune antibody is an antibody to a human retrovirus indicative of acquired immune deficiency syndrome (AIDS) or AIDS related complex (ARC).

4. The assay of claim 3, wherein the non-human immune antibody comprises IgG, IgM or mixtures thereof.

5. The assay of claim 4, wherein the non-human immune antibody is a procine immune antibody.

6. The assay of claim 1, wherein the non-human immune antibody is an antibody to HTLV-I.

7. The assay of claim 6, wherein the non-human immune antibody is a porcine immune antibody.

8. The assay of claim 6, wherein the non-human immune antibody comprises IgG, IgM or mixtures thereof.

9. The assay of claim 1, wherein the non-human immune antibody is an antibody to cytomegalovirus (CMV).

10. The assay of claim 9, wherein the non-human immune antibody is a porcine immune antibody.

11. The assay of claim 9, wherein the non-human immune antibody comprises IgG, IgM or mixtures thereof.

12. The assay of claim 1, wherein the virus is selected from the group consisting of HIV-1, HIV-2, HTLV-I, HTLV-II, cytomegalovirus, and Epstein Barr virus.

* * * * *

UNITED STATES PATENT AND TRADEMARK OFFICE
CERTIFICATE OF CORRECTION

PATENT NO. : 5,008,183
DATED : April 16, 1991
INVENTOR(S) : KURT B. OSTHER

It is certified that error appears in the above-identified patent and that said Letters Patent is hereby corrected as shown below:

The title page showing the illustrative figure should be deleted to be replaced with the attached title page.

Column 1, line 35: Change "activitY to --activity--.

Column 1, line 58 Change "tYpe" to --type--.

Column 8, lines 10-11 Change "procine" to --porcine--.

Column 8, line 34 Change "procine" to --porcine--.

Signed and Sealed this

Ninth Day of February, 1993

Attest:

STEPHEN G. KUNIN

Attesting Officer     Acting Commissioner of Patents and Trademarks

United States Patent [19]

Osther

[11] Patent Number: 5,008,183
[45] Date of Patent: Apr. 16, 1991

[54] ASSAY SYSTEM FOR DETECTING ANTIBODY AND A METHOD OF PRODUCING NON-HUMAN IMMUNE ANTIBODY

[75] Inventor: Kurt B. Osther, Dallas, Tex.

[73] Assignee: Bio-Research Laboratories, Inc., Dallas, Tex.

[21] Appl. No.: 192,241

[22] Filed: May 10, 1988

[51] Int. Cl.$^5$ .......................................... G01N 33/569
[52] U.S. Cl. ...................................... 435/5; 435/7.32; 436/513; 436/532; 436/547; 436/815; 530/387; 530/830
[58] Field of Search ............... 435/5, 7; 436/513, 532, 436/547, 815; 530/387, 830

[56] References Cited

U.S. PATENT DOCUMENTS

| | | | |
|---|---|---|---|
| 4,132,769 | 1/1979 | Osther | 436/543 |
| 4,474,877 | 10/1984 | Imagawa et al. | 436/513 X |
| 4,487,714 | 12/1984 | Kato et al. | 530/391 |
| 4,661,445 | 4/1987 | Saxinger et al. | 436/528 X |
| 4,725,669 | 2/1988 | Essex et al. | 530/395 X |
| 4,774,175 | 9/1988 | Chang et al. | 436/811 X |

OTHER PUBLICATIONS

Kalheider et al., "Porcine Immunoglobulins. I. Identification of Classes and Preparation of Specific Antisera", J. Immunol. 109(5)992-998 1972.

Thorn et al., "Enzyme Immunoassay Using Novel Recombinant . . . ", J. Clin., Microbiol. 25(7), 1207-1212 (Jul. 1987).

*Primary Examiner*—Christine Nucker
*Attorney, Agent, or Firm*—Bryan, Cave, McPheeters & McRoberts

[57] ABSTRACT

An improved assay method for detecting the presence of an antibody capable of binding with an antigen of a virus is provided. The improvement comprises using a non-human immune antibody which is reactive with an anti-human antibody as a positive control in the assay. Non-human immune IgM and a method of producing the IgM is also provided.

12 Claims, 1 Drawing Sheet